(12) United States Patent
Bodelin-Lecomte et al.

(10) Patent No.: US 6,235,295 B1
(45) Date of Patent: May 22, 2001

(54) METHOD FOR PREPARING A SOLID COSMETIC GYPSUM PLASTER BASED COMPOSITION AND RESULTING COSMETIC COMPOSITION

(75) Inventors: Sophie Bodelin-Lecomte, Vanves; Guénola Le Gars, Paris, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/180,674

(22) PCT Filed: Mar. 9, 1998

(86) PCT No.: PCT/FR98/00467

§ 371 Date: Feb. 8, 1999

§ 102(e) Date: Feb. 8, 1999

(87) PCT Pub. No.: WO98/40048

PCT Pub. Date: Sep. 17, 1998

(30) Foreign Application Priority Data

Mar. 13, 1997 (FR) .................................. 97/03168

(51) Int. Cl.$^7$ ...................................... A61K 9/14
(52) U.S. Cl. .............................. 424/401; 424/63
(58) Field of Search ....................... 424/401, 63

(56) References Cited

U.S. PATENT DOCUMENTS

| | | | |
|---|---|---|---|
| 4,724,138 | 2/1988 | Duffy et al. | 424/63 |
| 5,049,376 | * 9/1991 | Murphy et al. | 424/63 |
| 5,352,693 | 10/1994 | Farina | 514/398 |
| 5,510,107 | * 4/1996 | Lecomte et al. | 424/401 |

FOREIGN PATENT DOCUMENTS

| | | |
|---|---|---|
| 0 624 361 | 11/1994 | (EP) . |
| WO 86/00798 | 2/1986 | (WO) . |

OTHER PUBLICATIONS

English Language Derwent Abstract of EP 0 624 361.

* cited by examiner

*Primary Examiner*—Thurman K. Page
*Assistant Examiner*—T. Ware
(74) *Attorney, Agent, or Firm*—Finnegan, Henderson, Farabow, Garrett & Dunner, L.L.P.

(57) ABSTRACT

The invention relates to a process for the preparation of a plaster-based solid composition, in particular a cosmetic composition, this process comprising the following steps:

a pulverulent mixture comprising at least calcium sulphate hemihydrate in powder form is prepared, an aqueous phase is added to the pulverulent mixture, the pulverulent mixture and the aqueous phase are blended together so as to obtain a castable mixture, the castable mixture is poured into a mould, the mixture is left to cure by hydration of the calcium sulphate hemihydrate into calcium sulphate dihydrate, characterized in that a non-aqueous liquid preserving system is added to the pulverulent mixture before adding the aqueous phase. The invention also relates to a composition, in particular a cosmetic composition, which can be obtained by the process.

41 Claims, No Drawings

METHOD FOR PREPARING A SOLID COSMETIC GYPSUM PLASTER BASED COMPOSITION AND RESULTING COSMETIC COMPOSITION

This application is a 371 of PCT FR9800467 filed Mar. 9, 1998.

The present invention relates to a process for the manufacture of a solid composition using plaster, and to a composition, in particular a cosmetic composition, obtained by this process.

It is known practice to manufacture cosmetic compositions in solid form using plaster. These cosmetic compositions can be, in particular, eyeshadows, blushers, face powders or body powders. They can be in the form of sticks, pencils or cakes. The use of plaster to manufacture these solid compositions is described, for example, in patent U.S. Pat. No. 4,724,138. According to the known processes, a pulverulent phase containing plaster is mixed with an aqueous phase in order to obtain a paste which is shaped by moulding, the hydration reaction of the plaster (calcium sulphate hemihydrate) into calcium sulphate dihydrate leading to solidification of the composition. The use of plaster as a solidification agent is advantageous since it replaces the compacting operation, which is usually needed to obtain a composition in solid form from pulverulent products, with a moulding operation which is easier and less expensive to carry out and allows a wider range of forms to be obtained.

Moreover, it is common practice to add preserving agents to cosmetic compositions, with the aim of giving the composition good conservation, in particular to prevent the proliferation of microorganisms in the composition.

Preserving agents can be incorporated into plaster-based compositions in different ways. They can be added either to the pulverulent phase comprising the plaster, or to the aqueous phase before mixing these two phases together to form the castable paste. Thus, in patent U.S. Pat. No. 4,724,138, methyl para-hydroxybenzoate is added to the powder phase. Patent application WO 86/00798 proposes, for its part, to incorporate the preserving agents into the aqueous phase.

The Applicant has observed that when the preserving agents are added to the aqueous phase, the concentration of these preserving agents is not uniform in the final composition obtained after the water has been evaporated off, since there is a concentration gradient of the preserving agents in the final composition. The preserving agents are thus found to be concentrated towards the evaporation surface of the composition. Protection of the composition against the growth of microorganisms is thus not identical in all parts of the composition. In addition, when the composition is a make-up product, for example a blusher, application to the skin of that part of the composition containing the highest concentration of preserving agent can give rise to problems of tolerance of the composition on the skin: skin irritation or stinging can then be caused by too high a concentration of preserving agents in the composition applied.

It has also been observed that the concentration gradient of the preserving agents is also formed when a preserving agent in powder form is added, irrespective of the phase into which it is introduced.

The present invention is aimed at overcoming these drawbacks and proposes a process for the preparation of a composition, in particular a cosmetic composition, which makes it possible to obtain a uniform distribution of the preserving agents in the final composition. The term uniform distribution is understood to mean that the concentration of preserving agents is more or less constant in all parts of the final composition.

The Applicant has discovered, surprisingly and unexpectedly, that the use of a liquid preserving system makes it possible to obtain a composition with a uniform distribution of the preserving agent(s).

The subject of the present invention is thus a process for the preparation of a plaster-based solid composition, this process comprising the following steps:

a pulverulent mixture comprising at least calcium sulphate hemihydrate in powder form is prepared, an aqueous phase is added to the pulverulent mixture, the pulverulent mixture and the aqueous phase are blended together so as to obtain a castable mixture, the castable mixture is poured into a mould, the mixture is left to cure by hydration of the calcium sulphate hemihydrate into calcium sulphate dihydrate, characterized in that before adding the aqueous phase, a non-aqueous liquid preserving system comprising at least one preserving agent having a water-solubility of less than or equal to 0.5% at 25° C. (weight/weight percentage) is added to the pulverulent mixture, the said liquid preserving system having a viscosity of less than or equal to 4.5 Pa.s.

The invention also relates to a composition, in particular a cosmetic composition, which can be obtained by the process according to the invention. The composition thus obtained is entirely suitable for make-up. It can be used as a blusher, an eyeshadow or a face powder.

The invention also relates to a plaster-based solid cosmetic composition comprising a preserving system uniformly distributed in the said composition, the said preserving system being, when not in the composition, in the form of a non-aqueous liquid comprising at least one preserving agent having a water-solubility of less than or equal to 0.5% at 25° C., the said liquid preserving system having a viscosity of less than or equal to 4.5 Pa.s at 25° C.

The term preserving agent is understood to refer to any compound having antimicrobial and/or antioxidant action. A preserving agent having antimicrobial action is preferably used.

According to the present patent application, the expression non-aqueous liquid preserving system is understood to refer either to one or more preserving agents whose mixture is liquid at 25° C., or to one or more liquid or solid preserving agents, as a mixture with a non-aqueous solvent, the mixture being liquid at 25° C.

Preferably, the liquid preserving system according to the invention has a viscosity of less than 3 Pa.s at 25° C. and more preferably less than 1.5 Pa.s at 25° C.

The viscosity of the liquid preserving agent according to the invention can be measured, for example, on a Rheomat RM115 viscometer from Contraves, with a suitable rotor (for example MSDIN 108, 114, 125), at a shear rate of 221.3 5 $s^{-1}$, after 10 minutes.

It is necessary for the preserving system not to be aqueous, since the addition of the preserving agent to an aqueous phase does not give uniform distribution of the preserving agent in the final composition.

The liquid non-aqueous solvent according to the invention is any liquid compound which is compatible with the preserving agent, it being possible for the preserving agent or the mixture of preserving agents either to be dissolved, partially or totally, or to be dispersed uniformly in the said solvent at least at the time of use, i.e. the preserving agent or the mixture of preserving agents is well distributed in the solvent at the time of preparation of the mixture. Preferably, in particular when the preserving agent or the mixture of preserving agents is in powder form, the preserving agent or the mixture of preserving agents is dissolved, partially or totally, in the solvent. Thus, the mixture of preserving agent and of solvent should have the required viscosity according to the invention. The solvent for the preserving system is chosen such that it does not have a negative impact on the antimicrobial and/or antioxidant activity of the preserving agent.

Advantageously, a solvent for the preserving agent can be used which gives a solution of the preserving agent in the solvent (total dissolution of the preserving agent in the solvent). The preserving agent mixed with the said solvent is not necessarily liquid at 25° C. It can, in particular, be in powder form, but its water-solubility at 25° C. must be less than 0.5% (weight/weight percentage), preferably less than 0.4% and more preferably less than 0.35%.

Advantageously, a preserving system can be used comprising a preserving agent/solvent mixture in a preserving agent/solvent weight ratio ranging from about 10/90 to 90/10, and preferably from 20/80 to 40/60.

As liquid preserving agent, mention may be made of the mixture of isopropyl para-hydroxybenzoate, isobutyl para-hydroxybenzoate and n-butyl para-hydroxybenzoate (in the respective weight proportions of 40/30/30), sold under the name "Liquapar Oil" by the company ISP. This mixture of preserving agents is water-insoluble (water-solubility of less than 0.1% at 25° C.). This mixture of preserving agents can be mixed with a compatible solvent before being added to the pulverulent mixture. It can also be combined with another preserving agent while at the same time respecting the characteristics of the invention.

As non-liquid preserving agent having a water-solubility of less than 0.4% at 25° C., mention may be made of methyl para-hydroxybenzoate (solubility of 0.30%).

Advantageously, the content of preserving agent incorporated into the pulverulent mixture can range from 0.01% to 2% by weight relative to the weight of the pulverulent mixture, and preferably from 0.1% to 0.6%.

The calcium sulphate hemihydrate used according to the invention can be in its α form and/or in its β form. It can be mixed with at least one agent for modifying the setting time, such as retardants, for instance sodium citrate, or accelerators, for instance gypsum or sodium sulphates.

The amount of plaster present in the pulverulent mixture can range from 10% to 70% by weight relative to the total weight of the pulverulent mixture, preferably from 15% to 35% and more preferably from 20% to 30%.

In order to give the final composition good cohesion, at least one fatty substance can be added to the pulverulent phase. As fatty substances which can be used, mention may be made of mineral oils such as liquid petroleum jelly, oils of animal origin such as lanolin, oils of plant origin such as jojoba oil, esters of carboxylic acids and of $C_{10}$–$C_{22}$ fatty alcohol, esters of fatty acids and of alcohol, such as isopropyl palmitate, fatty alcohols, in particular $C_{10}$–$C_{22}$ fatty alcohols such as oleyl alcohol, isostearyl alcohol and octyldodecanol, synthetic oils such as hydrogenated or unhydrogenated poly(α-olefins), for instance polyisobutene (Parleam), polydecenes, silicone oils, in particular phenylsilicone oils, silicone gums or silicone waxes such as alkyldimethicones, and fluoro oils.

Preferably, the amount of fatty substance added to the pulverulent mixture can range from 0.1% to 20% by weight relative to the total weight of the pulverulent mixture, and preferably from 0.5% to 15%.

According to the first variant of the process according to the invention, the preserving system can be mixed with at least one fatty substance before being added to the pulverulent phase. In particular, the preserving system can result from mixing the preserving agent with at least one fatty substance, provided that this mixture is uniform, i.e. the preserving agent is well distributed in the fatty substance.

Advantageously, the mixture of para-hydroxybenzoates (Liquapar Oil) can be mixed with isopropyl palmitate, in a preserving agent/solvent weight/weight proportion ranging from 20/80 to 40/60.

The pulverulent mixture can advantageously comprise at least one surfactant to facilitate wetting and dispersion of the pulverulent mixture. The surfactant can be of nonionic nature, such as polyoxyethylenated sorbitan esters, of cationic nature such as quaternary ammonium salts, or of amphoteric nature such as betaine derivatives.

The amount of surfactant introduced into the pulverulent mixture can range from 0.1% to 10% by weight relative to the total weight of the pulverulent mixture.

According to a second variant of the process according to the invention, the surfactant present in the pulverulent mixture can be used as a solvent for the preserving system if it allows a compatible mixture to be obtained. It has been observed that polyoxyethylenated sorbitan esters are entirely suitable as solvent mixed with the preserving agent according to the invention.

Advantageously, the mixture of para-hydroxybenzoates (Liquapar Oil) can be mixed with sorbitan monolaurate polyoxyethylenated with 20 mol of ethylene oxide, sold under the name "Tween 20" by the company ICI. Methyl para-hydroxybenzoate and potassium sorbate can also be mixed with the Tween 20.

The pulverulent mixture can comprise at least one hydrophobic pulverulent material. This hydrophobic material in particular gives the final composition good cosmetic properties.

The term hydrophobic pulverulent material is understood to refer both to powders that are hydrophobic by nature (not treated by chemical grafting or coating) and to powders treated by chemical grafting or coating so as to give them hydrophobic properties.

In order to determine whether or not, according to the invention, a pulverulent material is hydrophobic, the test defined below is carried out. A test tube 20 mm in diameter is filled with 20 ml of water. 2 grams of powder are poured into the tube without stirring and the behaviour of the powder is observed for a maximum of 5 minutes. If the powder remains entirely at the surface, it is considered to be "hydrophobic". In the opposite case, it is considered to be "hydrophilic".

As powders which are hydrophobic by nature, mention may be made of talc (magnesium silicate hydrate), powders of hydrophobic polymers, such as the powder of polyamides such as Nylon, for instance the powder sold under the name "Orgasol 2002 ED NAT COS" by the company Atochem, polyethylene powder ("Coathylene HA 1681" from the company Plast Labor), expanded microspheres made of thermoplastic material ("Expancel 551 DE" from the company Casco Nobel), polyfluoro powders, in particular polytetrafluoro-ethylene powders ("MP 1400" from the company Du Pont de Nemours), silicone powders ("Tospearl" from the company Toshiba), powders of acrylic copolymers ("Polytrap Q5 6603 from the company Dow Chemical), polystyrene powders ("Polysphere 3000 SP" from the company Prespere), lipoamino acids such as lauroyllysine, boron nitride, metal soaps of $C_8$–$C_{22}$, more particularly $C_{12}$–$C_{18}$, carboxylic acids, for example zinc and magnesium stearates, zinc laurate or magnesium myristate.

The powders treated by chemical grafting or coating can be pulverulent products of either hydrophobic or hydrophilic nature, which have been treated with hydrophobic products, among which mention may be made, for example, of silicones, lipoamino acids, metal soaps, fluoro derivatives, mineral oils, lecithin, isopropyl triisostearoyl titanate, polyethylene and collagen and its derivatives.

The amount of hydrophobic pulverulent material introduced into the pulverulent mixture can range from 10% to 60% by weight relative to the total weight of the pulverulent mixture, and preferably from 20% to 45%.

According to a third variant of the process according to the invention, at least a fraction of the hydrophobic powder is mixed with the preserving system according to the invention before being added to the pulverulent phase. The preserving system is thus impregnated onto the hydrophobic powder before being incorporated into the pulverulent phase. This variant of the process according to the invention gives good distribution of the preserving agent in the final composition.

Preferably, as hydrophobic powder mixed with the said preserving system, polyamide powders of Nylon type can be used.

Advantageously, the paraben mixture, mixed with isopropyl palmitate or Tween 20, can be added with the Nylon powder "Orgasol 2002 ED NAT COS", and this powder thus impregnated can then be added to the pulverulent mixture comprising the plaster. In the same way, the methyl para-hydroxybenzoate and potassium sorbate, mixed with Tween 20 and with the Nylon powder, before being incorporated into the pulverulent mixture.

Instead of Nylon powder, the acrylic copolymer powder sold under the name "Polytrap Q5 6603" can also be used.

Besides the hydrophobic powders, the pulverulent phase can also comprise hydrophilic powders. The hydrophilic powders can be fillers and/or pigments.

Among the fillers, mention may be made of:

- micas, which are aluminium potassium silicates of varied compositions, of natural origin, such as muscovite, phlogopite, lepidolite, biotite and sericite, or of synthetic origin,
- bismuth oxychloride,
- silicas, which can be in the form of platelets or spheres, such as the silica sold under the name "Silica Beads SB 700" by the company Myoshi,
- hydrophilic polymer powders, which are of synthetic origin, such as polyacrylates, for example "Micropearl M 100" from the company Matsumoto, acrylic polyamides such as those sold by the company Oris, or polyurethanes such as "Plastic Powder D 800" from the company Toshnu, or which are of natural origin, such as cellulose or starch derivatives, for example porous cellulose microspheres,
- kaolin, which is an aluminium silicate hydrate,
- hydroxyapatite,
- zinc oxide or titanium oxide,
- calcium carbonate,
- magnesium carbonate and hydrocarbonate.

The hydrophilic treated fillers can be pulverulent materials treated by chemical grafting or coating to make their surface hydrophilic, using materials such as chitosan, titanium dioxide, silica or hydrophilic polymers, in particular sulphonic polyesters or quaternary polyammoniums.

The pigments can be any hydrophilic coloured pigment. These pigments can be inorganic pigments, organic pigments or pearlescent pigments, which may or may not be coated. Among the pigments, mention may be made of inorganic pigments such as optionally surface-treated titanium dioxide (rutile or anatase), black, yellow or red iron oxide, manganese violet, ultramarine blue, ultramarine violet, anhydrous or hydrated chromium oxide and ferric blue. The organic pigments can be chosen from carbon black, pigments of D & C type, and lakes based on cochineal carmine.

The pearlescent agents can be chosen from pearlescent pigments such as mica coated with organic and/or inorganic pigments such as titanium oxide or bismuth oxychloride, titanium mica coated with organic and/or inorganic pigments such as iron oxides, ferric blue or chromium oxide, and pearlescent pigments based on bismuth oxychloride.

The amount of hydrophilic pulverulent material introduced into the pulverulent mixture can range from 5% to 75% by weight relative to the total weight of the pulverulent mixture, and preferably from 25% to 60%.

Advantageously, the weight ratio of the amount of hydrophilic pulverulent material to the amount of hydrophobic material can range from 0.08 to 7.5 and preferably from 0.40 to 3.25.

The aqueous phase necessarily contains water in an amount which is sufficient to hydrate the plaster into calcium sulphate dihydrate. It can optionally comprise at least one water-soluble or water-dispersible additive. Additives which may be mentioned are water-soluble or water-dispersible polymers, surfactants and waxes. Cosmetic active agents can also be added to the aqueous phase, such as, for example, moisturizers such as glycerol or propylene glycol, or alternatively antioxidants or sunscreens.

The aqueous phase can be mixed with the pulverulent mixture in a pulverulent mixture/aqueous phase weight proportion ranging from 0.2 to 2 and preferably from 0.5 to 1.5, so as to obtain a castable mixture.

When the paste obtained by mixing the pulverulent mixture and the aqueous phase is cast in a mould, the mixture is left to cure at room temperature. In order to accelerate the setting time, it is possible to leave the paste to dry by placing the moulds in a chamber heated to a temperature which can be, for example, up to 25° C. When the final composition is fully dry, it can be used directly in its mould. The composition can also be removed from the mould and placed in suitable packaging.

Examples illustrating the present invention without, however, limiting it will now be given.

EXAMPLE 1

(invention)

A preserving system (A) was prepared by mixing 17.73 g of methyl para-hydroxybenzoate and 82.27 g of sorbitan monolaurate polyoxyethylenated with 20 mol of ethylene oxide (Tween 20 from ICI).

This preserving system has a viscosity of 0.58 Pa.s, measured at 24.9° C. on a Rheomat RM115 viscometer from Contraves, with the MSDIN 114 rotor, at a shear rate of 221.3 s$^{-1}$.

A pulverulent mixture having the formulation below was then prepared:

| | |
|---|---|
| calcium sulphate hemihydrate | 25 g |
| hydrophilic powders | 29.8 g |
| hydrophobic powders | 33.7 g |
| fatty substances | 6 g |
| pigments | 3.4 g |

-continued

| | |
|---|---|
| preserving system (A) | 2.1 g |

125 g of water were added to the pulverulent mixture and the mixture was then blended until a castable paste was obtained. The paste was then poured into dishes, and then dried.

The product obtained after drying is in the form of a cake and can be taken up easily using a powder puff.

The methyl para-hydroxybenzoate content was measured in two separate areas of the dry composition. To do this, some of the composition was taken from the surface of the cake and some from the bottom of the cake. For each part taken, the preserving agent was extracted in a manner known to those skilled in analytical chemistry and was assayed by standard techniques of liquid chromatography.

The following assay results were obtained:
para-hydroxybenzoate concentration at the surface: 0.29%
para-hydroxybenzoate concentration at the bottom: 0.27%

It is thus seen that the preserving agent concentration is more or less identical in the two analysed areas of the cake. The preserving agent is thus uniformly distributed in the composition obtained.

EXAMPLE 2
(invention)

A composition was prepared in a similar manner to that of Example 1, except that the preserving system (A) was mixed with Nylon powder before being added to the pulverulent mixture.

To do this, a pulverulent preparation P1 comprising 4.94 g of methyl para-hydroxybenzoate, 22.92 g of Tween 20 and 72.14 g of Nylon powder (Orgasol 2002 ED NAT COS) were thus mixed together.

A pulverulent mixture having the formulation below was then prepared:

| | |
|---|---|
| calcium sulphate hemihydrate | 25 g |
| hydrophilic powders | 29.8 g |
| hydrophobic powders | 28.3 g |
| silicone-containing fatty substances | 6 g |
| pigments | 3.4 g |
| pulverulent preparation P1 | 7.5 g |

125 g of water were added to the pulverulent mixture and the mixture was then blended until a castable paste was obtained. The paste was then poured into dishes, and then dried.

The product obtained after drying is in the form of a cake and can be taken up easily using a powder puff.

The following preserving agent concentrations were obtained:

| | |
|---|---|
| surface of the cake: | 0.26% |
| bottom of the cake: | 0.26% |

A composition having a uniform concentration of preserving agent is thus obtained.

EXAMPLE 3
(comparative)

A composition more or less the same as that of Example 1 was prepared, but the preserving agent was introduced directly into the pulverulent mixture.

The pulverulent mixture prepared had the following composition:

| | |
|---|---|
| calcium sulphate hemihydrate | 25 g |
| hydrophilic powders | 27.4 g |
| hydrophobic powders | 29.52 g |
| silicone-containing fatty substances | 6 g |
| pigments | 3.4 g |
| fragrance | 0.21 g |
| Tween 20 | 1 g |
| methyl para-hydroxybenzoate (powder) | 0.37 g |

125 g of water were added to the pulverulent mixture and the mixture was then blended until a castable paste was obtained. The paste was then poured into dishes, and then dried.

The product obtained after drying is in the form of a cake.

The following preserving agent concentrations were obtained:

| | |
|---|---|
| surface of the cake: | 0.22% |
| bottom of the cake: | 0.58% |

A composition with a higher preserving agent concentration at the bottom of the composition and a lower preserving agent concentration at the surface of the composition is thus obtained. The distribution of the preserving agent in the composition is thus not substantially identical.

EXAMPLE 4
(comparative)

A composition more or less the same as that of Example 1 was prepared, but the preserving agent was introduced directly into the aqueous phase.

The pulverulent mixture prepared had the following composition:

| | |
|---|---|
| calcium sulphate hemihydrate | 25 g |
| hydrophilic powders | 27.4 g |
| hydrophobic powders | 29.89 g |
| silicone-containing fatty substances | 6 g |
| pigments | 3.4 g |
| fragrance | 0.21 g |
| Tween 20 | 1 g |

An aqueous phase comprising 42.38 g of demineralized water and 0.21 g of methyl para-hydroxybenzoate was added to the pulverulent mixture.

After drying, a cake was obtained in which the preserving agent concentration is higher at the bottom and lower at the surface of the composition.

EXAMPLE 5
(invention)

Working in the same way as in Example 1, a preserving system (B) was prepared by mixing together 40 g of preserving agent Liquapar Oil and 60 g of Tween 20. This preserving system has a viscosity of 0.77 Pa.s, measured at 25.3° C. on a Rheomat RM115 viscometer from Contraves, with the MSDIN 108 rotor, at a shear rate of 221.3 s$^{-1}$. The pulverulent mixture having the composition below was then prepared:

| | |
|---|---:|
| calcium sulphate hemihydrate | 25 g |
| hydrophilic powders | 29.8 g |
| hydrophobic powders | 34.87 g |
| silicone-containing fatty substances | 6 g |
| pigments | 3.4 g |
| preserving system (B) | 0.93 g |

125 g of water were added to the pulverulent mixture and the mixture was then blended until a castable paste was obtained. The paste was then poured into dishes, and then dried.

The product obtained after drying is in the form of a cake.

The following preserving agent concentrations were obtained:

| | |
|---|---:|
| surface of the cake: | 0.35% |
| bottom of the cake: | 0.34% |

A composition with a more or less constant preserving agent concentration is thus obtained.

EXAMPLE 6

A composition more or less identical to that of Example 5 was prepared, but the solvent for the preserving system was changed.

A preserving system (C) was thus prepared by mixing together 26.62 g of Liquapar Oil and 73.38 g of isopropyl palmitate. This preserving system has a viscosity of 0.023 Pa.s, measured at 25.8° C. on a Rheomat RM115 viscometer from Contraves, with the MSDIN 125 rotor, at a shear rate of $221.3 \text{ s}^{-1}$. The pulverulent mixture having the composition below was then prepared:

| | |
|---|---:|
| calcium sulphate hemihydrate | 25 g |
| hydrophilic powders | 29.8 g |
| hydrophobic powders | 34.41 g |
| fatty substances | 6 g |
| pigments | 3.4 g |
| preserving system (C) | 1.39 g |

The product obtained after drying is in the form of a cake and can be taken up easily using a powder puff.

The following preserving agent concentrations were obtained:

| | |
|---|---:|
| surface of the cake: | 0.34% |
| bottom of the cake: | 0.37% |

A composition having a uniform concentration of preserving agent is thus obtained.

EXAMPLE 7
(invention)

A composition similar to that of Example 2 was prepared, but using Liquapar Oil as preserving agent.

The viscosity of the preserving system, measured under the same conditions as those of Example 1, is less than 0.77 Pa.s.

A cake having the following preserving agent concentrations was obtained:

| | |
|---|---:|
| surface of the cake: | 0.34% |
| bottom of the cake: | 0.35% |

A composition having a homogeneous concentration of preserving agents is thus obtained.

EXAMPLE 8
(comparative)

A composition was prepared in the same way as in Example 2, but using chlorphenesine which is a preserving agent with a water-solubility of 0.6% at 25° C.

To do this, a pulverulent preparation P2 comprising 6.4 g of chlorphenesine, 20.3 g of Tween 20 and 73.3 g of Nylon powder (Orgasol 2002 ED NAT COS) was thus mixed up.

A pulverulent mixture having the formulation below was then prepared:

| | |
|---|---:|
| calcium sulphate hemihydrate | 25 g |
| hydrophilic powders | 27.4 g |
| hydrophobic powders | 26.1 g |
| silicone-containing fatty substances | 6 g |
| pigments | 10.5 g |
| pulverulent preparation P2 | 5 g |

125 g of water were added to the pulverulent mixture and the mixture was then blended until a castable paste was obtained. The paste was then poured into dishes, and then dried.

The product obtained after drying is in the form of a cake.

The following preserving agent concentrations were obtained:

| | |
|---|---:|
| surface of the cake: | 0.219% |
| bottom of the cake: | 0.588% |

It was thus observed that with a preserving agent having a water-solubility of greater than 0.5% at 25° C., a composition with a higher preserving agent concentration at the bottom of the composition and a lower preserving agent concentration at the surface of the composition is obtained. The distribution of the preserving agent in the composition is thus not substantially identical.

EXAMPLE 9
(invention)

A preserving system (D) was prepared by mixing together Tween 20 and Liquapar Oil and this preserving system was then mixed with acrylic copolymer powder. The viscosity of the preserving system, measured under the same conditions as those of Example 1, is less than 0.77 Pa.s.

To do this, a pulverulent preparation P3 comprising 4.94 g of Liquapar Oil, 13.54 g of Tween 20 and 81.52 g of acrylic copolymer powder (Polytrap Q5 6603) was thus mixed together.

A pulverulent mixture having the formulation below was then prepared:

| | |
|---|---:|
| calcium sulphate hemihydrate | 25 g |
| hydrophilic powders | 29.3 g |

| | |
|---|---|
| hydrophobic powders | 28.3 g |
| silicone-containing fatty substances | 6 g |
| pigments | 3.4 g |
| pulverulent preparation P3 | 7.5 g |

25 g of water were added to the pulverulent mixture and the mixture was then blended until a castable paste was obtained. The paste was then poured into dishes, and then dried.

The product obtained after drying is in the form of a cake and can be taken up easily using a powder puff.

The following preserving agent concentrations re obtained:

| | |
|---|---|
| surface of the cake: | 0.34% |
| bottom of the cake: | 0.30% |

A composition having a uniform concentration of preserving agent is thus obtained.

What is claimed is:

1. A process for the preparation of a plaster-based solid cosmetic composition, said process comprising:
   preparing a pulverulent mixture comprising at least calcium sulphate hemihydrate in powder form,
   adding to the pulverulent mixture a non-aqueous liquid preserving system having a viscosity of less than or equal to 4.5 pascal seconds, hereinafter abbreviated Pa.s, at 25° C. and comprising at least one preserving agent having a water-solubility of less than or equal to 0.5% at 25° C.,
   adding an aqueous phase to the pulverant mixture,
   blending together the pulverulent mixture and the aqueous phase to obtain a castable mixture,
   pouring the castable mixture into a mold, and,
   curing the castable mixture by hydration of the calcium sulphate hemihydrate into calcium sulphate dihydrate.

2. A process according to claim 1, wherein said liquid preserving system has a viscosity of less than or equal to 3 Pa.s at 25° C.

3. A process according to claim 1, wherein said liquid preserving system comprises at least two preserving agents.

4. A process according to claim 1, wherein said liquid preserving system comprises a mixture of at least one preserving agent and a non-aqueous liquid solvent.

5. A process according to claim 4, wherein said at least one preserving agent is dissolved, partially or totally, in said solvent.

6. A process according to claim 1, wherein said at least one preserving agent comprises isopropyl para-hydroxybenzoate, isobutyl para-hydroxybenzoate and n-butyl para-hydroxybenzoate.

7. A process according to claim 1, wherein said at least one preserving agent is methyl para-hydroxybenzoate.

8. A process according to claim 1, wherein said at least one preserving agent is present in the pulverulent mixture in an amount ranging from 0.01% to 2% by weight, relative to the total weight of the pulverulent mixture.

9. A process according to claim 1, further comprising adding at least one fatty substance to the pulverulent mixture.

10. A process according to claim 9, wherein said at least one fatty substance is chosen from a mineral oil, a plant oil, an oil of animal origin, and a synthetic oil.

11. A process according to claim 9, wherein said at least one fatty substance is chosen from a hydrogenated or unhydrogenated poly($\alpha$-olefin), a phenylsilicone oil, and an ester of a fatty acid and of $C_1$–$C_8$ alcohol.

12. A process according to claim 9, wherein said at least one fatty substance is isopropyl palmitate.

13. A process according to claim 9, wherein said at least one fatty substance is present in the pulverulent mixture in an amount ranging from 0.1% to 20% by weight relative to the total weight of the pulverulent mixture.

14. A process according to claim 4, wherein said non-aqueous liquid solvent is a fatty substance, wherein said fatty substance is chosen from a mineral oil, a plant oil, an oil of animal origin, a synthetic oil, a hydrogenated or unhydrogenated poly($\alpha$-olefin), a phenylsilicone oil, an ester of a fatty acid and of $C_1$–$C_8$ alcohol, and isopropyl palmitate.

15. A process according to claim 1, wherein said pulverulent mixture comprises at least one hydrophobic pulverulent material.

16. A process according to claim 15, wherein said at least one hydrophobic pulverulent material is a powder treated by chemical grafting or coating chosen from powders treated with silicones, lipoamino acids, metal soaps, fluoro derivatives, mineral oils, lecithin, isopropyl triisostearoyl titanate, polyethylene and collagen and its derivatives.

17. A process according to claim 15, wherein said at least one hydrophobic pulverulent material is a powder which is hydrophobic by nature, selected from talc, a hydrophobic polymer powder, a lipoamino acid, boron nitride and a metal soap of $C_8$–$C_{22}$ carboxylic acids.

18. A process according to claim 16, wherein said at least one hydrophobic pulverulent powder is chosen from a polyamide powder, a polyethylene powder, an expanded microsphere made of a thermoplastic material, a polyfluoro powder, a silicone powder, an acrylic copolymer and a polystyrene powder.

19. A process according to claim 15, wherein said at least one hydrophobic pulverulent material is present in said pulverulent mixture in an amount ranging from 10% to 60% by weight relative to the total weight of the pulverulent mixture.

20. A process according to claim 19, wherein said at least one hydrophobic pulverulent material is present in an amount ranging from 20% to 45% by weight relative to the total weight of the pulverulent mixture.

21. A process according to claim 15, further comprising mixing said preserving system with said at least one hydrophobic pulverulent material before adding said preserving system to said pulverulent mixture.

22. A process according to claim 21, wherein said at least one hydrophobic pulverulent material is chosen from Nylon powder and an acrylic copolymer.

23. A process according to claim 1, wherein the pulverulent mixture comprises at least one hydrophilic pulverulent material.

24. A process according to claim 23, wherein said at least one hydrophilic pulverulent material is chosen from a pigment and a filler.

25. A process according to claim 23, wherein said at least one hydrophilic pulverulent material is present in the pulverulent mixture in an amount ranging from 5% to 75% by weight relative to the total weight of the pulverulent mixture.

26. A process according to claim 25, wherein said at least one hydrophilic pulverulent material is present in the pulverulent mixture in an amount ranging from 25% to 60% by weight relative to the total weight of the pulverulent mixture.

27. A process according to claim 1, wherein said pulverulent mixture comprises at least one hydrophilic pulverulent material and at least one hydrophobic pulverulent material and the weight ratio of the amount of hydrophilic pulverulent material to the amount of hydrophobic material ranges from 0.08 to 7.5.

28. A process according to claim 27, wherein said weight ratio ranges from 0.40 to 3.25.

29. A process according to claim 1, wherein the pulverulent mixture further comprises at least one surfactant.

30. A process according to claim 29, wherein said at least one surfactant is present in the pulverulent mixture in an amount ranging from 0.1% to 10% by weight relative to the weight of the pulverulent mixture.

31. A process according to claim 4, wherein said non-aqueous liquid solvent is a surfactant.

32. A process according to claim 29, wherein said at least one surfactant is a polyoxyethylenated sorbitan ester.

33. A process according to claim 1, wherein the calcium sulphate hemihydrate is present in the pulverulent mixture in an amount ranging from 10% to 70% by weight relative to the total weight of the pulverulent mixture.

34. A process according to claim 33, wherein said calcium sulphate hemihydrate is present in the pulverulent mixture in an amount ranging from 15% to 35% by weight relative to the total weight of the pulverulent mixture.

35. A process according to claim 1, wherein the pulverulent mixture and the aqueous phase are blended together in a weight ratio ranging from 0.2 to 2.

36. A process according to claim 35, wherein the pulverulent mixture and the aqueous phase are blended together in a weight ratio ranging from 0.5 to 1.5.

37. A composition made by the process according to claim 1.

38. A plaster-based solid cosmetic composition comprising a preserving system uniformly distributed in said composition, said preserving system being, when not in the composition, in the form of a non-aqueous liquid comprising at least one preserving agent having a water-solubility of less than or equal to 0.5% at 25° C., said liquid preserving system having a viscosity of less than or equal to 4.5 Pa.s at 25° C.

39. A process according to claim 31, wherein said surfactant is polyoxyethylenated sorbitan ester.

40. A process according to claim 31, wherein the water-solubility of said at least one preserving agent is less than 0.35%.

41. A process according to claim 9, further comprising mixing said at least one fatty substance with said non-aqueous liquid preserving system, and then adding the mixture of said at least one fatty substance and said preserving system to the pulverulent mixture.

* * * * *

UNITED STATES PATENT AND TRADEMARK OFFICE
CERTIFICATE OF CORRECTION

PATENT NO.    : 6,235,295 B1
DATED         : May 22, 2001
INVENTOR(S)   : Sophie Bodelin-Lecomte et al.

Page 1 of 1

It is certified that error appears in the above-identified patent and that said Letters Patent is hereby corrected as shown below:

Title page,
Item [57], ABSTRACT, line 9, "mould" should read -- mold --.

Column 11,
Line 35, "pulverant" should read -- pulverulent --.

Column 14,
Line 17, "claim 31" should read -- claim 1 --.

Signed and Sealed this

Thirtieth Day of April, 2002

Attest:

JAMES E. ROGAN
*Attesting Officer*  *Director of the United States Patent and Trademark Office*